Figure 1:
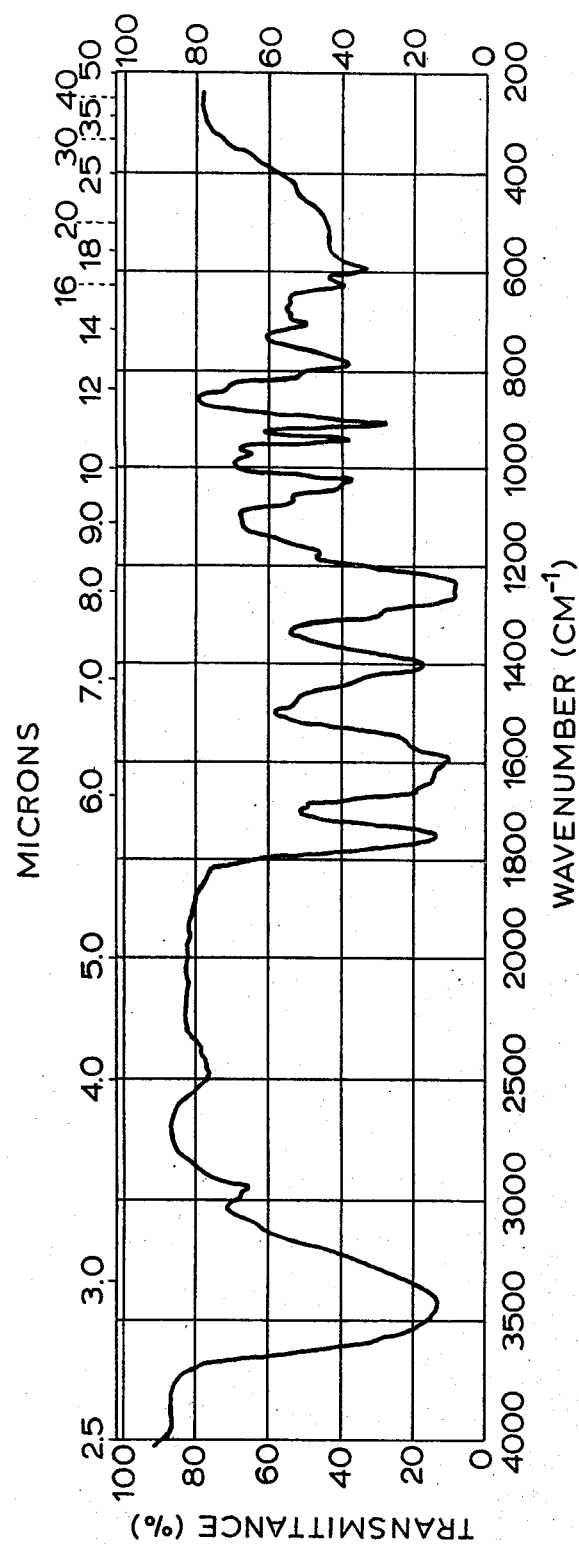

United States Patent [19]

Box et al.

[11] 4,179,498

[45] Dec. 18, 1979

[54] STREPTOMYCETAL ANTIBIOTIC

[75] Inventors: Stephen J. Box, Plummers Plain Nr. Horsham; John D. Hood, Cranleigh, both of England

[73] Assignee: Beecham Group Limited, England

[21] Appl. No.: 717,336

[22] Filed: Aug. 24, 1976

Related U.S. Application Data

[63] Continuation-in-part of Ser. No. 664,917, Mar. 8, 1976, abandoned.

[30] Foreign Application Priority Data

Mar. 15, 1975 [GB] United Kingdom ............ 10914/75

[51] Int. Cl.² ............................................ A61K 25/00
[52] U.S. Cl. ............................ 424/117; 260/326.2; 435/902; 435/121

[58] Field of Search .................. 424/117; 260/326.31; 195/80 R

[56] References Cited

U.S. PATENT DOCUMENTS

| | | | |
|---|---|---|---|
| 3,919,415 | 11/1975 | Butterworth et al. | 424/115 |
| 3,950,357 | 4/1976 | Kattan et al. | 260/326.27 |

*Primary Examiner*—Jerome D. Goldberg
*Attorney, Agent, or Firm*—Jacobs & Jacobs

[57] ABSTRACT

A novel antibiotic designated herein MM 17880 may be obtained from the cultivation of strains of *Streptomyces olivaceus* and related organisms. In addition to being potent antibacterial agents, MM 17880 and its salts inhibit β-lactamase obtained from many organisms so that it shows a synergistic antibacterial effect when combined with β-lactam antibiotics.

9 Claims, 3 Drawing Figures

STREPTOMYCETAL ANTIBIOTIC

CROSS REFERENCE

This application is a continuation-in-part of U.S. Patent application Ser. No. 664,917 filed Mar. 8, 1976, now abandoned.

BACKGROUND TO THE INVENTION

British Pat. No. 1363075 disclosed that strains of *Streptomyces olivaceus* are able to produce a useful β-lactamase inhibiting substance. Belgian Pat. Nos. 827331 and 827332 showed that the material of British Pat. No. 1363075 was highly impure and contained only small quantities of antibacterially active agents. These antibacterially active agents were characterised in the Belgian Patents and were designated MM 4550 MM 13902. We have now found that in addition to MM 4550 and MM 13902, certain strains of *Streptomyces olivaceus* and related organisms produce a further antibacterially active β-lactamase inhibiting compound. This new material is designated herein as MM 17880. Nothing herein should be construed as claiming any material disclosed in the aforementioned British of Belgian Patents or any process for the preparation of any such material. Other antibacterial agents are known to be produced by strains of Streptomyces, for example those disclosed in German Offenlegungsschrift No. 2340005 and that designated Thienamycin as disclosed in U.S. Pat. No. 3950357 and which was said to have the structural formula:

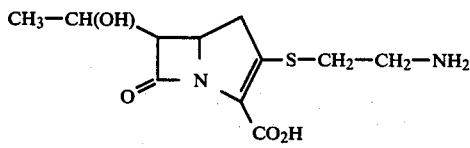

Based on the present knowledge of the structure of MM 17880 significant structural differences are apparent between thienamycin and MM 17880.

DESCRIPTION OF THE INVENTION

The present invention provides MM 17880 and salts thereof which substance MM 17880 is a di-acidic solid which in the form of a substantially pure di-sodium salt has the following properties:

(a) It has a characteristic infra-red spectrum which when taken in a KBr disc is substantially as shown in FIG. 1.

Figure 2:
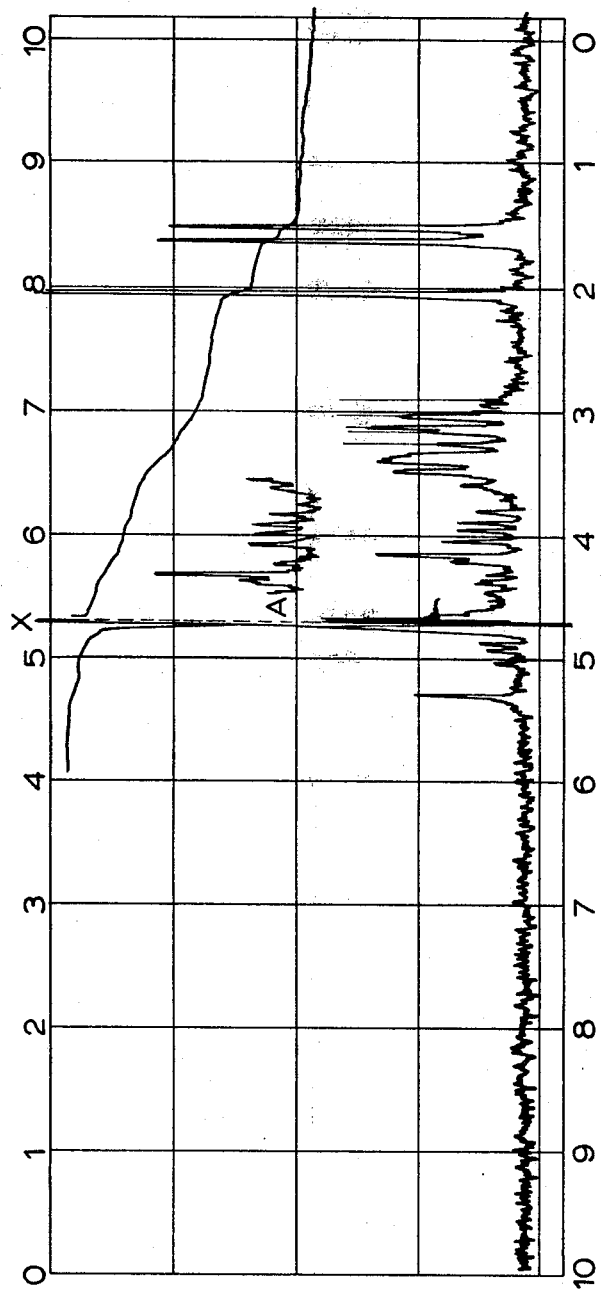

(b) It has a characteristic nuclear magnetic resonance spectrum which when taken in deuterium oxide is substantially as shown in FIG. 2.

Figure 3:
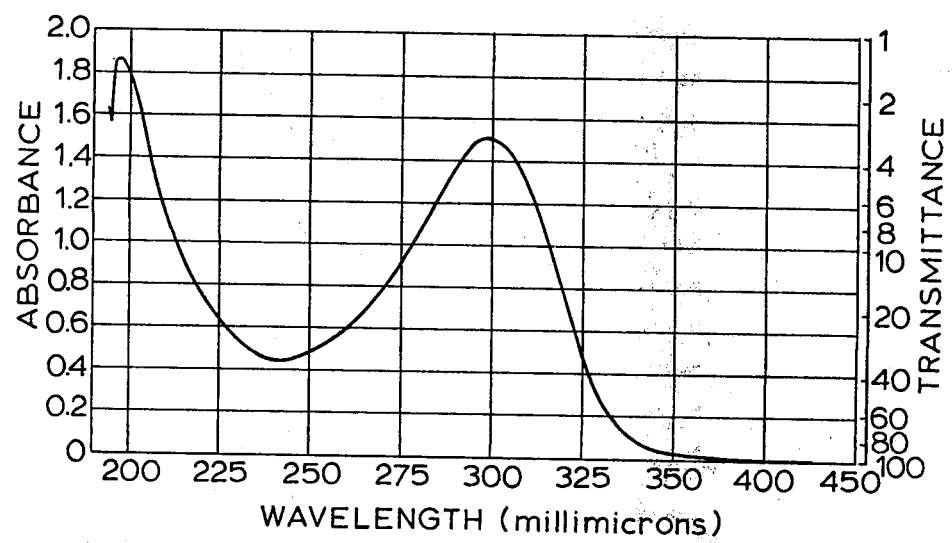

(c) It has a characteristic ultra-violet spectrum which in water has an absorption maximum at about 297 nm substantially as shown in FIG. 3.

It is believed that one of the acidic groups in the MM 17880 is a carboxylic acid group. When substantially pure, MM 17880 as a di-sodium salt has the $R_f$ values in the thin layer chromatography systems given in Table 1.

Table 1

| Support | Rf values of MM 17880 Di-Sodium Salt | |
|---|---|---|
| | Solvent System | Rf |
| cellulose** | butanol/isopropanol/water 7/7/6 | 0.7 |
| cellulose** | n/propanol/water 4/1 | 0.7 |

Table 1-continued

| Support | Rf values of MM 17880 Di-Sodium Salt | |
|---|---|---|
| | Solvent System | Rf |
| cellulose** | isopropanol/water 7/3 | 0.8 |
| silica gel* | n/butanol/methanol/water 4/1/2 | 0.4 |
| silica gel* | n/propanol/0.1M phosphate 7/3 buffer pH 7.0 | 0.6 |

*the silica gel plates were Merck $F_{254}$ plates.
**the cellulose plates were Eastman Kodak 13255.

It is likely that MM 17880 contains sulphur and nitrogen is addition to carbon, oxygen and hydrogen. It is likely that MM 17880 has a molecular weight between 300 and 500. Elemental analysis indicates that the di-sodium salt of MM 17880 has a molecular formula $C_{11-14}H_{16-21}O_8$-$_{11}N_2S_2Na_2$. Thus MM 17880 has the molecular formula $C_{11-14}H_{18-23}O_8$-$_{11}N_2S_2$. It is believed that MM 17880 has the structural formula:

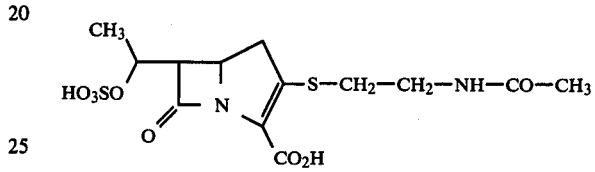

When substantially pure, MM 17880 as a di-sodium salt has a good level of antibacterial activity when determined by the microtitre method against certain gram-positive and gram-negative organisms, for example, against strains of *Bacillus subtilis, Enterobacter cloacae, Escherichia coli, Klebsiella aerogenes, Proteus mirabilis, Salmonella typhimurium, Serratia marcescens* and *Staphylococcus aureus*.

When substantially pure, MM 17880 as a di-sodium salt is able to synergyse the anti-bacterial activity of β-lactam antibiotics such as ampicillin, and amoxycillin and the like against certain bacteria including certain β-lactamase producing strains of *Staphylococcus aureus* and *Klebsiella aerogenes*.

When used herein the term "substantially pure" means at least 75% pure and preferably at least 85% pure, for example, 90–100% pure.

In general the salts of MM 17880 are much more stable than the unsalted acid which tends to decompose in solution.

The di-basic salts of MM 17880 provided by this invention are preferably pharmaceutically acceptable salts such as sodium, potassium, calcium, magnesium, aluminium or conventional ammonium or substituted ammonium salts.

Most suitably this invention provides pharmaceutically acceptable alkali metal salts of MM 17880, for example, a di-sodium or di-potassium salt of MM 17880.

In a further aspect this invention provides pharmaceutical compositions which contain MM 17880 or a pharmaceutically acceptable salt thereof.

Such compositions are suitable for combating bacterial infection or for prophylaxis in mammals including humans. For example, the compositions of this invention may be used in the treatment of diseases of the respiratory tract, urinary tract, soft tissues, skin and the like. For use in such treatments the compositions may be provided in conventional form for oral, topical, intra-mammary, injectable or infusable presentation.

In a preferred aspect this invention provides a pharmaceutical composition which contains MM 17880 or a pharmaceutically acceptable salt thereof which composition is adapted for oral or parenteral administration to humans.

Such preferred compositions will generally contain from 10 mg. to 5 g of MM 17880 or a salt thereof and will more usually contain 50 mg. to 1.25 g of a salt of MM 17880, for example, 150 mg. to 1.0 g.

The compositions of this invention may contain MM 17880 or a salt thereof as sole therapeutic agent or they may contain MM 17880 or a salt thereof together with other therapeutic agents, for example, a penicillin or cephalosporin such as ampicillin, amoxycillin, carbenicillin, benzylpenicillin, in-vivo hydrolysable esters of any of the preceding penicillins, phenoxymethylpenicillin, cephaloridine, cephalothin, cephaloglycin, cephamandol, cephazolin, acetone or formaldehyde adducts of any of the preceding penicillins or cephalosporins which contain an $\alpha$-amino group in the acylamino side chain, cloxacillin, dicloxacillin, flucloxacillin or other conventional $\beta$-lactam antibiotics.

The compositions of this invention may contain carriers in conventional manner as will be understood to those skilled in the preparation of anti-bacterial compositions.

A further aspect of this invention provides a process for the preparation of MM 17880 or a salt thereof which process comprises cultivation of an MM 17880 producing strain of *Streptomyces olivaceus* and isolating MM 17880 or a salt thereof from the mixture.

Cultivation of *Streptomyces olivaceus* may be carried out as described in British Patent No. 1363075 or Belgian Patents Nos. 827331 and 827332 and will generally involve aerobic fermentation in the presence of assimilable sources of carbon, nitrogen, sulphur and mineral salts. The required nutrients may be provided by complex organic sources or by chemically defined media in conventional manner.

When used herein, the term "*Streptomyces olivaceus*" is defined according to the classification of Hutter R (in Systematic der Streptomyceten, S. Korger, Basle, Pages 8–32). Note that on this definition *Streptomyces fulvovoridis, Streptomyces flavus* and *Streptomyces flavovirens* may be regarded as being synonymous with *Streptomyces olivaceus*.

The spore morphology and carbon utilisation characteristics of "*Streptomyces olivaceus*" are described in Belgian Patents Nos. 827331 and 827332.

The preferred organism for use in this process is *Streptomyces olivaceus* ATCC 31126 or mutants thereof.

An alternative aspect of this invention comprises the preparation of substantially pure MM 17880 or a salt thereof by isolation of the said MM 17880 or salt thereof from a crude antibacterial complex obtained by (a) the cultivation of a MM 17880 producing strain of *Streptomyces olivaceus* or related species followed by (b) the extraction of crude antibacterial complex from the cultivation medium. MM 17880 is normally obtained mainly from the culture filtrate so that the preferred initial step in the isolation procedure is the removal of solid material from the fermentation, for example, by filtration.

In general, all isolation and purification procedures should take place at non-elevated temperatures, for example, below 20° C. and more suitably not above 12° C.

The impure MM 17880 or salt may be obtained from the clarified culture filtrate by adsorbing the MM 17880 or salt thereof into a material such as active carbon and then eluting with aqueous acetone and evaporating off the solvents under reduced pressure. The crude product from this process may be purified further by dissolving in water and extracting into an organic phase using a lipophilic quaternary ammonium salt to form an organic solvent soluble salt followed by back extraction into water or dilute sodium iodide or the like.

Alternatively, the culture filtrate may be extracted using a lipophilic quaternary ammonium salt and an organic solvent followed by back extraction into aqueous sodium iodide solution or the like. This is frequently more effective than the process which uses intermediate concentration of the filtrate.

We believe that the chromatographic purification of MM 17880 is best carried out using a salt of MM 17880 such as the sodium salt. Salts of MM 17880 are normally more soluble in aqueous and aqueous/alcohol solvent systems than in highly lipophilic solvents consequently it is preferred to use aqueous and aqueous/alcohol solvent systems in the chromatographic purifications used in this invention.

In our hands, aqeous solutions of electrolytes buffered to approximate neutrality have proved suitable for use in conjunction with polar support materials such as basic ion-exchange resins for the purification of MM 17880. Thus an aqueous solution of sodium chloride buffered to about pH 7 with a conventional buffer such as phosphate buffer may be used in conjunction with support materials which contain quaternary ammonium groups. We have found that basic ion-exchange celluloses and basic ion-exchange cross linked dextrans are suitable support materials and that QAE Sephadex A25 (Sephadex is a registered trademark) in particular is a highly suitable support material.

Separation of MM 17880 from inorganic salts in particular but also from other contaminating substances may be achieved by adsorbing the antibiotic to a lipophilic resin to which inorganic salts are not adsorbed. In our hands a polystyrene-divinylbenzene co-polymer such as Amberlite XAD-4 is particularly suitable, the desired antibiotic may be removed from the column by elution (elution with water or aqueous alkanol) and the resulting solution concentrated by evaporation and freeze dried to yield a material of improved purity. Separation of MM 17880 from inorganic salts may also suitably be carried out by chromatography on a column composed of a gel filtration agent for example corsslinked dextran gels such as Sephadex G15 and polyacrylamide gels such as Biogel P2.

Further purification of MM 17880 from materials prepared using one or more of the processes described above may be carried out by column chromatography on an inert solid phase such as silica gel or cellulose using aqueous alcoholic solvent systems. Suitable solvent systems will contain water and at least one lower alkanol, for example, water/isopropanol, water/n-propanol, water/methanol/isopropanol, water/butanol, water/ethanol/butanol or similar systems. In our hands a 4/1 mixture of n-propanol and water has proved to be a particularly suitable solvent system to use in conjunction with a cellulose support.

The fractions to be collected and retained are those showing a u.v. spectrum characteristic of MM 17880 (see for example, FIG. 3) which has an u.v. absorption maximum at about 297 mm. The freeze drying of the resultant solution yields a substantially pure salt of MM 17880.

From the preceeding information, it will be realized that from one view-point, the present invention provides a process for the preparation of substantially pure MM 17880 or a salt thereof which process comprises the chromatographic separation of a solution containing MM 17880 or a salt thereof together with further antibacterial materials into fractions consisting essentially of a solution of MM 17880 or a salt thereof and recovering the substantially pure MM 17880 or salt thereof from solution.

Such a process normally involves column chromatography using an inert support such as cellulose and an alkanolic solvent system as previously described.

The following Examples illustrate this invention.

EXAMPLE 1

Preparation of Substantially Pure MM 17880 Sodium Salt a. Fermentation

*Streptomyces olivaceus* ATCC 31126 was grown for 7 days at 28° C. on a solid agar slant in a Roux bottle. The agar medium had the following composition:

| Constituent | Amount (g/l) |
| --- | --- |
| Yeast Extract | 10.0 |
| Glucose Monohydrate | 10.0 |
| Agar | 15.0 |
| Tap Water | to 1 l |

[The "Yeast extract" was "Yeatex" as supplied by Bovril Food Ingredients, P.O. Box 18, Wellington Road, Burton-on-Trent and the "Agar" was supplied by Oxoid Limited, Southwark Bridge Road, London, S.E.1.].

The medium was adjusted to pH 6.8 before sterilisation. 50 ml. of sterile deionised water containing 0.02% Tween 80 (Registered Trade Mark) was added to one Roux bottle culture and the spores suspended by shaking. This spore suspension was then added as inoculum to 75 l of sterilised seed stage medium in a 100 l stainless steel fermenter. The composition of the seed stage medium was as follows:

| Constituent | Amount (g/l) |
| --- | --- |
| Soya-bean Flour | 10.0 |
| Glucose Monohydrate | 20.0 |
| Tap Water | to 1 l |

[The "Soya-bean Flour" was Arkasoy 50 as supplied by the British Arkady Co. Ltd., Old Trafford, Manchester].

To control foaming 50 ml. of 10% v/v Pluronic L81 (Registered Trade Mark) is soya-bean oil was added to the fermentation medium before sterilisation. [Pluronic L81 was supplied by Jacobsen van den Berg U.K. Ltd., 231 The Vale, London, W.3.]. The medium was steam sterilised in the fermenter for 20 mins at 120° C. The seed stage culture was stirred at 140 r.p.m. with a 7.5 inch diameter vaned disc agitator and supplied with 75 l/min sterile air through an open ended sparger. The culture vessel was fitted with baffles. The temperature was controlled at 28° C. and after incubation under these conditions for 45 hours, 7.5 l of this seed culture was added as inoculum to 150 l sterile fermentation medium in a 300 l stainless steel fermenter. The fermentation medium had the following composition:

| Constituent | Amount (g/l) |
| --- | --- |
| Soya-bean Flour (Arkasoy 50) | 10.0 |
| Glucose Monohydrate | 20.0 |
| Chalk (Precipitated Calcium Carbonate | 0.2 |
| Sodium Sulphate | 10.0 |
| Cobalt Chloride (CoCl$_2$,6H$_2$O) | 0.001 |
| Tap Water | to 1 l |

300 ml. of 10% Pluronic L81 in soya-bean oil was added to prevent foaming. The fermentation was harvested after 48 hours and clarified by centrifugation. The clarified brew was arbitarily assigned an activity of 340 units/ml when assayed by the conventional hole in plate method on agar seeded with *Klebsiella aerogenes*.

b. Isolation of Substantial Pure MM 17880 as a Sodium Salt

Clarified brew prepared essentially as in (a) (1050 l; 340 units/ml) at 10° C. and pH 6.8 was extracted with dichloromethane (310 l) at 10° C. containing cetyldimethylbenzylammonium chloride (1200 g) by pumping the two liquids at predetermined flow rates through an in-line mixer. The phases were separated in a Sharples continuous centrifuge having been admixed for about two minutes. The dichloromethane phase (300 l) was back-extracted with aqueous sodium iodide. The back-extraction was performed in four batches using a total of 7 l water containing 210 g sodium iodide. The phases were separated by gravity. The aqueous phase was adjusted from pH 7.7 to pH 7.0 with hydrochloric acid and filtered. The sodium iodide extract (7 l) contained 21,900 units/ml.

An ion exchange column was prepared by packing QAE Sephadex A25 (supplied by Pharmacia Ltd) in pH 7 phosphate buffer (0.05 M) containing sodium chloride (0.3 M) into a 10 cm diameter glass column to a height of 40 cm. The sodium iodide extract (7 l) at 5° C. was percolated through the QAE Sephadex at 50 ml/min. The column was eluted with 0.7 M NaCl in 0.05 M phosphate buffer, pH 7 also at 5° C. at a flow rate of 25 ml/min. 2 l eluate was discarded and 90 fractions (100 ml) were collected. The fractions were scanned in a u.v. spectrophotometer and those showing an absorption maximum at about 285 nm, which were found to contain a mixture of MM 17880 and an impurity that was responsible for the absorption at 285 nm, were pooled and adjusted to pH 7 (fraction numbers 25–35, pooled volume 1230 ml at 8450 units/ml).

Sodium chloride (5 g/100 ml) was added to the pooled fraction which were then percolated at 5° C. through a 6.3 cm diameter column packed with Amberlite XAD 4 resin (supplied by Rohm & Haas Lts) to a height of 30 cm at a flow rate of 20 ml/min. The antibiotic was adsorbed to the resin under these conditions whereas the inorganic impurities were not. The antibiotic was eluted at room temperature with distilled water (200 ml.) followed by 50% aqueous methanol. The eluate (1 l.) was evaporated below 30° C. under reduced pressure to 70 ml., adjusted to pH 7 and freeze dried to a brown solid (2.18 g.) at 5000 units/mg. Another batch of the material produced by the above process was slightly purer having an activity of 5700 units/mg. This solid (0.55 g) was chromatographed on a cellulose column (4×29 cm) (Whatman CC 31) equilibrated with n-propanol/water (4/1). The column was eluted with n-propanol/water (4/1), the first 135 ml. of eluant were discarded then 15 ml. fractions collected. Those fractions with a u.v. absorption spectrum characteristic of MM 17880 were combined (45 ml.), evaporated under reduced pressure to remove n-propanol then freeze dried to yield a yellow solid (33 mg.). The solid was assayed at an activity of 16,000 units/mg.

EXAMPLE 2

The fermentation and isolation procedure was followed essentially as described in Example 1, up to and including the elution from Amberlite XAD-4. The eluate from the Amberlite XAD-4 column was concentrated under reduced pressure to approximately 20 ml volume. This solution was run onto a QAE Sephadex A25 column (3.8×30 cm) prepared in 0.18 M NaCl. The column was eluted initially with an exponential gradient of sodium chloride from 0.18 to 0.28 M over a total volume of 2 liters followed by elution at a constant sodium chloride composition of 0.28 M. The column was eluted at 4° C. at a rate of 3 ml/min. and 25 ml fractions were collected. Fractions with a u.v. absorption spectrum characteristic of MM 17880 (90-105) were bulked (400 ml).

The combined fractions were evaporated under reduced pressure to approximately 10 ml and loaded onto a 3.8×28 cm column of Biogel P2 (200-400 mesh) (Bio Rad Laboratories) equilibrated in 1% butanol. The column was eluted with 1% butanol at a rate of 2 ml/min. and 5 ml fractions were collected. Fractions with a u.v. absorption spectrum characteristic of MM 17880 and giving a negative silver nitrate reaction for chloride were combined. The combined fractions were evaporated in vacuo to remove butanol and freeze dried to yield an amorphous solid (73 mg).

The solid (70 mg) was dissolved in a minimum of n-propanol/water (4/1) and run onto a cellulose column (1.5×15 cm) (Whatman CC 31) equilibrated in the same solvent mixture. The column was eluted with n-propanol/water (4/1) at 1 ml/min., 6 ml fractions were collected. Fractions were monitored for their u.v. absorption spectra and those with a spectrum characteristic of MM 17880 (13-16) were combined (24 ml) evaporated under reduced pressure to remove propanol and freeze dried to yield a light brown amorphous solid (17 mg).

Properties of MM 17880 Sodium Salt Produced as Above

The material produced essentially as described in Example 2 had the i.r., n.m.r. and u.v. spectra shown in FIGS. 1, 2 and 3 respectively.

The antibacterial activity of the material produced as above was determined by the microtitre method using the overnight inoculum of the test organism at 0.2% concentration. The results are shown in Table 2. The synergistic activity of the di-sodium salt of MM 17880 in combination with ampicillin and with cephaloridine against *Klebsiella aerogenes* and *Staphylococcus aureus* Russell are shown in Table 3.

The di-sodium salt of MM 17880 so produced had an $I_{50}$ of $250 \times 10^{-12}$ g/ml against the β-lactamase from *E. coli* JT4 when determined by the method of Belgian Patent No. 827331.

Electrophoresis suggests that the material produced is a di-sodium salt so that MM 17880 is a di-acid.

An elemental analysis carried out on a sample of the di-sodium salt of MM 17880 produced as above gave the following results:
C:31.9%; H:4.2%; N:5.4%; S:13.2%; Na:11.6%
It should be remembered that the material subjected to analysis was prepared by freeze-drying and so may contain water or other impurites. The di-sodium salt of MM 17880 contains (in addition to carbon, hydrogen and oxygen) the elements sulphur, nitrogen and sodium in the ratio 2:2:2 so that the molecular formula of the di-sodium salt based on the analysis is $C_{11-14}$, $H_{16-21}$, $O_{8-11}$, $N_2$, $S_2$, $Na_2$.

The spectral properties of the di-sodium salt of MM 17880 suggest that the material contains a fused β-lactam.

TABLE 2

ANTIBACTERIAL ACTIVITY OF MM 17880 AGAINST A RANGE OF ORGANISMS (MIC μg/ml)

| Organism | MM 17880 |
|---|---|
| *Bacillus subtilis* | 0.2 |
| *Citrobacter freundii* Mantio | 3.1 |
| *Enterobacter cloacae* P99 | 12.5 |
| *E. coli* 10418 | 0.1 |
| *E. coli* JT4 | 3.1 |
| *Klebsiella aerogenes* A | 0.8 |
| *Klebsiella aerogenes* Ba95 | 12.5 |
| *Proteus mirabilis* 13 | 1.6 |
| *Proteus morganii* I580 | 1.6 |
| *Proteus rettgeri* WM16 | 0.2 |
| *Proteus vulgaris* W090 | 0.2 |
| *Pseudomonas aeruginosa* A | >50 |
| *Salmonella typhimurium* CT10 | 0.2 |
| *Serratia marcescens* US1 | 0.4 |
| *Staphylococcus aureus* Oxford | 0.4 |
| *Staphylococcus aureus* Russell | 0.4 |
| *Streptococcus faecalis* I | 6.2 |
| *Streptococcus pyogenes* CN10 | <0.04 |

TABLE 3

ACTIVITY OF MM 17880 IN COMBINATION WITH AMPICILLIN AND CEPHALORIDINE (MIC μg/ml)

| Compound or Combination | Klebsiella aerogenes A | Staphylococcus aureus Russell |
|---|---|---|
| MM 17880 alone | 0.2 | 3.1 |
| Ampicillin alone | 250 | 500 |
| Ampicillin + 17880 .02μ | 50 | 6.2 |
| Ampicillin + 17880 .1μ | 1.25 | 0.6 |
| Ampicillin + 17880 .5μ | — | 0.07 |
| Cephaloridine alone | 5.0 | 1.25 |
| Cephaloridine + 17880 .02μ | 1.25 | 0.3 |
| Cephaloridine + 17880 .1μ | 1.0 | 0.06 |
| Cephaloridine + 17880 .5μ | — | 0.015 |

TABLE 4

ANTIBACTERIAL ACTIVITY OF THE DT-SODIUM SALT OF MM 17880 (MICROTITRE METHOD - HEAVY INOCULUM, 1/100 OVERNIGHT BROTH)

| Organism | MIC (mg/ml) |
|---|---|
| *Bacillus subtilis* A | 0.19 |
| *Staph. aureus* Oxford | 0.78 |
| *Staph. aureus* Russell | 0.78 |
| *Enterobacter cloacae* N1 | 25 |
| *E. coli* 10418 | <0.19 |
| *Kleb. aerogenes* A | 0.19 |
| *Ps. aeruginose* A | >200 |
| *Salmonella typhimurium* CT 10 | 0.19 |
| *Serratia marcescens* US 39 | 1.56 |

What we claim is:

1. A pharmaceutically acceptable di-basic salt of MM 17880 which is at least 75% pure wherein MM 17880 is a di-acidic solid of the molecular formula $C_{11-14}H_{18-23}O_{8-11}N_2S_2$ which in the form of a substantially pure di-sodium salt, has the following properties:
  (a) when present at 0.4% w/w in a freshly prepared KBr disc, it has a characteristic infra-red spectrum substantially as shown in FIG. 1;

(b) it has a characteristic nuclear magnetic resonance spectrum which when taken in deuterium oxide is substantially as shown in FIG. 2;

(c) it has a characteristic ultra-violet spectrum which in water has an absorption maximum at about 297 n.m. substantially as shown in FIG. 3;

(d) it possesses antibacterial activity against certain gram-positive and gram-negative organisms, including strains of *Bacillus subtilis, Enterobacter cloacae, Escherichia coli, Klebsiella aerogenes, Proteus mirabilis, Salmonella typhimurium, Serratia marcescens* and *Staphylococcus aureus;* and (e) when mixed with ampicillin or amoxycillin it synergizes their antibacterial activity against certain bacteria, including strains of *Staphylococcus aureus* and *Klebsiella aerogenes.*

2. A pharmaceutically acceptable di-basic salt of MM 17880 according to claim 1 in the form of an alkali metal salt.

3. A pharmaceutically acceptable di-basic salt of MM 17880 according to claim 1 in the form of the sodium, potassium, calcium, magnesium, aluminium or ammonium salt.

4. A pharmaceutically acceptable di-basic salt of MM 17880 according to claim 1 in the form of the di-sodium salt.

5. A pharmaceutically acceptable di-basic salt of MM 17880 according to claim 1 in the form of the di-potassium salt.

6. A pharmaceutically acceptable di-basic salt of MM 17880 according to claim 1 which is at least 85% pure.

7. A pharmaceutically acceptable di-basic salt of MM 17880 according to claim 1 which is 90%–100% pure.

8. A process for the preparation of a pharmaceutically acceptable di-basic salt of MM 17880, which is at least 75% pure wherein MM 17880 is a di-acidic solid of the molecular formula $C_{11-14}H_{18-23}O_{8-11}N_2S_2$ which in the form of a substantially pure di-sodium salt, has the following properties:

(a) when present at 0.4% w/w in a freshly prepared KBr disc, it has a characteristic infra-red spectrum substantially as shown in FIG. 1;

(b) it has a characteristic nuclear magnetic resonance spectrum which when taken in deuterium oxide is substantially as shown in FIG. 2;

(c) it has a characteristic ultra-violet spectrum which in water has an absorption maximum at about 297 n.m. substantially as shown in FIG. 3;

(d) it possesses antibacterial activity against certain gram-positive and gram-negative organisms, including strains of *Bacillus subtilis, Enterobacter cloacae, Escherichia coli, Klebsiella aerogenes, Proteus mirabilis, Salmonella typhimurium, Serratia marcescens* and *Staphylococcus aureus;* and (e) when mixed with ampicillin or amoxycillin it synergizes their antibacterial activity against certain bacteria, including strains of *Staphylococcus aureus* and *Klebsiella aerogenes,* which comprises cultivating an MM 17880 producing strain of *Streptomyces olivaceus* having the same identifying characteristics as ATCC 31126 in a suitable medium containing an assimilable source of carbon, hydrogen, sulphur and nitrogen until a significant amount of antibiotic activity has been imparted to said medium and recovering the pharmaceutically acceptable di-basic salt of MM 17880 from the culture medium.

9. A process according to claim 8 wherein MM 17880 is isolated in the form of a pharmaceutically acceptable di-basic salt by extracting the di-basic salt into an aqueous lower alkanol solvent followed by chromatographic purification.

* * * * *